(12) United States Patent
Komp et al.

(10) Patent No.: US 12,064,191 B2
(45) Date of Patent: Aug. 20, 2024

(54) SURGICAL TOOL NAVIGATION USING SENSOR FUSION

(71) Applicant: Covidien LP, Mansfield, MA (US)

(72) Inventors: John W. Komp, Dillon, CO (US); Seth Gleiman, Guilford, CT (US); Scott E. M. Frushour, Boulder, CO (US); Nathan J. Knutson, Long Lake, MN (US)

(73) Assignee: Covidien LP, Mansfield, MA (US)

( * ) Notice: Subject to any disclaimer, the term of this patent is extended or adjusted under 35 U.S.C. 154(b) by 92 days.

(21) Appl. No.: 17/315,207

(22) Filed: May 7, 2021

(65) Prior Publication Data

US 2021/0378759 A1  Dec. 9, 2021

Related U.S. Application Data

(60) Provisional application No. 63/034,081, filed on Jun. 3, 2020.

(51) Int. Cl.
*A61B 34/20* (2016.01)
*A61B 90/00* (2016.01)

(52) U.S. Cl.
CPC .............. *A61B 34/20* (2016.02); *A61B 90/36* (2016.02); *A61B 2034/2055* (2016.02); *A61B 2034/2061* (2016.02); *A61B 2562/0219* (2013.01); *A61B 2562/0233* (2013.01)

(58) Field of Classification Search
CPC . A61B 34/20; A61B 90/36; A61B 2034/2055; A61B 2034/2061; A61B 2562/0219; A61B 2562/0233; A61B 90/361; A61B 1/2676; A61B 2017/00699; A61B 2017/00703; A61B 2034/105; A61B 34/25; A61B 90/37; A61B 2034/2048; A61B 2090/363; A61B 2090/364; A61B 2090/376; A61B 2090/3784
See application file for complete search history.

(56) References Cited

U.S. PATENT DOCUMENTS

| | | | |
|---|---|---|---|
| 4,202,352 A | 5/1980 | Osborn | |
| 5,358,496 A | 10/1994 | Ortiz et al. | |
| 6,086,586 A | 7/2000 | Hooven | |
| 6,533,784 B2 | 3/2003 | Truckai et al. | |

(Continued)

FOREIGN PATENT DOCUMENTS

| | | |
|---|---|---|
| BR | 0013237 A | 7/2003 |
| BR | 0116004 A | 6/2004 |

(Continued)

OTHER PUBLICATIONS

Extended European Search Report issued in European Patent Application No. 21177465.8 dated Oct. 8, 2021, 10 pages.

*Primary Examiner* — Alexei Bykhovski
(74) *Attorney, Agent, or Firm* — Weber Rosselli & Cannon LLP

(57) ABSTRACT

A system and method for a catheter in a luminal network including capturing images via an optical sensor, comparing the captured images to pre-operative images, identifying fiducials in the captured images that correspond to fiducials in the pre-operative images; and depicting the position of the catheter in a three-dimensional (3D) model or two-dimensional (2D) images derived from the pre-operative images.

19 Claims, 6 Drawing Sheets

(56) References Cited

U.S. PATENT DOCUMENTS

| | | |
|---|---|---|
| 6,656,177 B2 | 12/2003 | Truckai et al. |
| 6,802,843 B2 | 10/2004 | Truckai et al. |
| 6,835,336 B2 | 12/2004 | Watt |
| 6,913,579 B2 | 7/2005 | Truckai et al. |
| 7,947,000 B2 | 5/2011 | Vargas et al. |
| 8,335,359 B2 | 12/2012 | Fidrich et al. |
| 8,706,184 B2 | 4/2014 | Mohr et al. |
| 8,827,934 B2 | 9/2014 | Chopra et al. |
| 9,226,799 B2 | 1/2016 | Lightcap et al. |
| 9,304,018 B2 | 4/2016 | Davis et al. |
| 9,459,087 B2 | 10/2016 | Dunbar et al. |
| 9,597,008 B2 | 3/2017 | Henkel et al. |
| 9,743,896 B2 | 8/2017 | Averbuch |
| 9,801,630 B2 | 10/2017 | Harris et al. |
| 9,918,659 B2 | 3/2018 | Chopra et al. |
| 10,159,530 B2 | 12/2018 | Lang |
| 10,172,973 B2 | 1/2019 | Vendely et al. |
| 10,200,677 B2 | 2/2019 | Trevor et al. |
| 10,206,686 B2 | 2/2019 | Swayze et al. |
| 10,251,708 B2 | 4/2019 | Baldauf et al. |
| 10,317,196 B2 | 6/2019 | Laine et al. |
| 10,349,938 B2 | 7/2019 | Widenhouse et al. |
| 10,373,719 B2 | 8/2019 | Soper et al. |
| 10,376,178 B2 | 8/2019 | Chopra |
| 10,405,753 B2 | 9/2019 | Sorger |
| 10,478,162 B2 | 11/2019 | Barbagli et al. |
| 10,480,926 B2 | 11/2019 | Froggatt et al. |
| 10,484,669 B2 | 11/2019 | Trevor et al. |
| 10,524,866 B2 | 1/2020 | Srinivasan et al. |
| 10,555,788 B2 | 2/2020 | Panescu et al. |
| 10,610,306 B2 | 4/2020 | Chopra |
| 10,638,953 B2 | 5/2020 | Duindam et al. |
| 10,674,970 B2 | 6/2020 | Averbuch et al. |
| 10,682,070 B2 | 6/2020 | Duindam |
| 10,706,543 B2 | 7/2020 | Donhowe et al. |
| 10,709,506 B2 | 7/2020 | Coste-Maniere et al. |
| 10,716,637 B2 | 7/2020 | Kowshik et al. |
| 10,729,886 B2 | 8/2020 | Fenech et al. |
| 10,743,751 B2 | 8/2020 | Landey et al. |
| 10,772,485 B2 | 9/2020 | Schlesinger et al. |
| 10,779,803 B2 | 9/2020 | Prisco et al. |
| 10,792,022 B2 | 10/2020 | Keast et al. |
| 10,792,464 B2 | 10/2020 | Romo et al. |
| 10,796,432 B2 | 10/2020 | Mintz et al. |
| 10,823,627 B2 | 11/2020 | Sanborn et al. |
| 10,827,913 B2 | 11/2020 | Ummalaneni et al. |
| 10,835,153 B2 | 11/2020 | Rafii-Tari et al. |
| 10,856,855 B2 | 12/2020 | Gordon |
| 10,881,385 B2 | 1/2021 | Fenech |
| 10,885,630 B2 | 1/2021 | Li et al. |
| 2003/0013972 A1 | 1/2003 | Makin |
| 2005/0020878 A1 | 1/2005 | Ohnishi et al. |
| 2005/0165276 A1 | 7/2005 | Belson et al. |
| 2006/0235457 A1 | 10/2006 | Belson |
| 2007/0135803 A1 | 6/2007 | Belson |
| 2012/0089014 A1 | 4/2012 | Sabczynski et al. |
| 2013/0096385 A1 | 4/2013 | Fenech et al. |
| 2013/0261633 A1 | 10/2013 | Thornberry |
| 2013/0303945 A1 | 11/2013 | Blumenkranz et al. |
| 2014/0035798 A1 | 2/2014 | Kawada et al. |
| 2014/0052018 A1 | 2/2014 | Hawkins |
| 2014/0235943 A1 | 8/2014 | Paris et al. |
| 2015/0148690 A1 | 5/2015 | Chopra et al. |
| 2015/0265368 A1 | 9/2015 | Chopra et al. |
| 2016/0001038 A1 | 1/2016 | Romo et al. |
| 2016/0067450 A1 | 3/2016 | Kowshik |
| 2016/0157939 A1 | 6/2016 | Arkin et al. |
| 2016/0183841 A1 | 6/2016 | Duindam et al. |
| 2016/0192860 A1 | 7/2016 | Allenby et al. |
| 2016/0278746 A1 | 9/2016 | Hancu et al. |
| 2016/0287344 A1 | 10/2016 | Donhowe et al. |
| 2016/0331358 A1 | 11/2016 | Gordon |
| 2016/0370177 A1 | 12/2016 | Laine et al. |
| 2016/0374676 A1 | 12/2016 | Flanagan et al. |
| 2017/0020628 A1 | 1/2017 | Averbuch |
| 2017/0055940 A1 | 3/2017 | Shoham |
| 2017/0112576 A1 | 4/2017 | Coste-Maniere et al. |
| 2017/0112588 A1 | 4/2017 | Bissing et al. |
| 2017/0157361 A1* | 6/2017 | Barrish ............ A61M 25/0155 |
| 2017/0209071 A1* | 7/2017 | Zhao ................. A61B 1/00006 |
| 2017/0224338 A1 | 8/2017 | Sung |
| 2017/0238795 A1 | 8/2017 | Blumenkranz et al. |
| 2017/0258309 A1 | 9/2017 | Deyanov |
| 2017/0265952 A1 | 9/2017 | Donhowe et al. |
| 2017/0273665 A1 | 9/2017 | Kapoor et al. |
| 2017/0274189 A1 | 9/2017 | Smith et al. |
| 2017/0296292 A1 | 10/2017 | Mahmood et al. |
| 2017/0311844 A1 | 11/2017 | Zhao et al. |
| 2017/0319165 A1 | 11/2017 | Averbuch |
| 2017/0354470 A1 | 12/2017 | Farritor et al. |
| 2018/0001058 A1 | 1/2018 | Schlesinger |
| 2018/0049808 A1 | 2/2018 | Krimsky |
| 2018/0064904 A1 | 3/2018 | Vargas et al. |
| 2018/0078318 A1 | 3/2018 | Barbagli et al. |
| 2018/0085135 A1 | 3/2018 | Singh et al. |
| 2018/0110569 A1 | 4/2018 | Drain |
| 2018/0153621 A1 | 6/2018 | Duindam et al. |
| 2018/0185100 A1 | 7/2018 | Weinstein et al. |
| 2018/0214138 A9 | 8/2018 | Prisco et al. |
| 2018/0221039 A1 | 8/2018 | Shah |
| 2018/0235709 A1 | 8/2018 | Donhowe et al. |
| 2018/0240237 A1 | 8/2018 | Donhowe et al. |
| 2018/0250004 A1 | 9/2018 | Williams et al. |
| 2018/0256262 A1 | 9/2018 | Duindam et al. |
| 2018/0263706 A1 | 9/2018 | Averbuch |
| 2018/0279852 A1 | 10/2018 | Rafii-Tari et al. |
| 2018/0325419 A1 | 11/2018 | Zhao et al. |
| 2018/0333209 A1 | 11/2018 | Frushour et al. |
| 2018/0368656 A1* | 12/2018 | Austin ................. A61B 1/051 |
| 2018/0368917 A1* | 12/2018 | Dekel .................. A61B 1/009 |
| 2019/0000559 A1 | 1/2019 | Berman et al. |
| 2019/0000560 A1 | 1/2019 | Berman et al. |
| 2019/0008413 A1 | 1/2019 | Duindam et al. |
| 2019/0011709 A1 | 1/2019 | Yadav et al. |
| 2019/0038365 A1 | 2/2019 | Soper et al. |
| 2019/0053858 A1 | 2/2019 | Kapoor et al. |
| 2019/0056202 A1 | 2/2019 | Bortolami et al. |
| 2019/0065209 A1 | 2/2019 | Mishra et al. |
| 2019/0076143 A1 | 3/2019 | Smith |
| 2019/0076203 A1 | 3/2019 | Ang et al. |
| 2019/0090955 A1 | 3/2019 | Singh et al. |
| 2019/0110839 A1 | 4/2019 | Rafii-Tari et al. |
| 2019/0142374 A1 | 5/2019 | Kruecker et al. |
| 2019/0143513 A1 | 5/2019 | Rabindran et al. |
| 2019/0175062 A1 | 6/2019 | Rafii-Tari et al. |
| 2019/0183318 A1 | 6/2019 | Froggatt et al. |
| 2019/0183585 A1 | 6/2019 | Rafii-Tari et al. |
| 2019/0183587 A1 | 6/2019 | Rafii-Tari et al. |
| 2019/0192143 A1 | 6/2019 | Shelton, IV et al. |
| 2019/0192234 A1 | 6/2019 | Gadda et al. |
| 2019/0200984 A1 | 7/2019 | Shelton, IV et al. |
| 2019/0209016 A1 | 7/2019 | Herzlinger et al. |
| 2019/0209043 A1 | 7/2019 | Zhao et al. |
| 2019/0216548 A1 | 7/2019 | Ummalaneni |
| 2019/0223693 A1 | 7/2019 | Vargas |
| 2019/0223759 A1* | 7/2019 | Page .................... A61B 34/35 |
| 2019/0231443 A1 | 8/2019 | McGinley et al. |
| 2019/0231449 A1 | 8/2019 | Diolaiti et al. |
| 2019/0239723 A1 | 8/2019 | Duindam et al. |
| 2019/0239724 A1 | 8/2019 | Averbuch et al. |
| 2019/0239831 A1 | 8/2019 | Chopra |
| 2019/0246876 A1 | 8/2019 | Schaning |
| 2019/0250050 A1 | 8/2019 | Sanborn et al. |
| 2019/0254649 A1 | 8/2019 | Walters et al. |
| 2019/0269470 A1 | 9/2019 | Barbagli et al. |
| 2019/0269885 A1 | 9/2019 | Bailey et al. |
| 2019/0272634 A1 | 9/2019 | Li et al. |
| 2019/0290375 A1 | 9/2019 | Dearden et al. |
| 2019/0298160 A1 | 10/2019 | Ummalaneni et al. |
| 2019/0298451 A1 | 10/2019 | Wong et al. |
| 2019/0320878 A1 | 10/2019 | Duindam et al. |
| 2019/0320937 A1 | 10/2019 | Duindam et al. |
| 2019/0328213 A1 | 10/2019 | Landey et al. |
| 2019/0336238 A1 | 11/2019 | Yu et al. |

(56) References Cited

U.S. PATENT DOCUMENTS

| | | |
|---|---|---|
| 2019/0343424 A1 | 11/2019 | Blumenkranz et al. |
| 2019/0350659 A1 | 11/2019 | Wang et al. |
| 2019/0365199 A1 | 12/2019 | Zhao et al. |
| 2019/0365479 A1 | 12/2019 | Rafii-Tari |
| 2019/0365486 A1 | 12/2019 | Srinivasan et al. |
| 2019/0380787 A1 | 12/2019 | Ye et al. |
| 2020/0000319 A1 | 1/2020 | Saadat et al. |
| 2020/0000526 A1 | 1/2020 | Zhao |
| 2020/0008655 A1 | 1/2020 | Schlesinger et al. |
| 2020/0008827 A1 | 1/2020 | Dearden et al. |
| 2020/0022767 A1 | 1/2020 | Hill et al. |
| 2020/0029948 A1 | 1/2020 | Wong et al. |
| 2020/0030044 A1 | 1/2020 | Wang et al. |
| 2020/0030461 A1 | 1/2020 | Sorger |
| 2020/0030575 A1 | 1/2020 | Bogusky et al. |
| 2020/0038750 A1 | 2/2020 | Kojima |
| 2020/0043207 A1 | 2/2020 | Lo et al. |
| 2020/0046431 A1 | 2/2020 | Soper et al. |
| 2020/0046436 A1 | 2/2020 | Tzeisler et al. |
| 2020/0054399 A1 | 2/2020 | Duindam et al. |
| 2020/0060771 A1 | 2/2020 | Lo et al. |
| 2020/0069192 A1 | 3/2020 | Sanborn et al. |
| 2020/0069384 A1 | 3/2020 | Fenech et al. |
| 2020/0077870 A1 | 3/2020 | Dicarlo et al. |
| 2020/0077991 A1 | 3/2020 | Gordon et al. |
| 2020/0078095 A1 | 3/2020 | Chopra et al. |
| 2020/0078103 A1 | 3/2020 | Duindam et al. |
| 2020/0085514 A1 | 3/2020 | Blumenkranz |
| 2020/0100776 A1 | 4/2020 | Blumenkranz et al. |
| 2020/0107894 A1 | 4/2020 | Wallace et al. |
| 2020/0109124 A1 | 4/2020 | Pomper et al. |
| 2020/0121170 A1 | 4/2020 | Gordon et al. |
| 2020/0129045 A1 | 4/2020 | Prisco |
| 2020/0129239 A1 | 4/2020 | Bianchi et al. |
| 2020/0138515 A1 | 5/2020 | Wong |
| 2020/0146757 A1 | 5/2020 | Fenech et al. |
| 2020/0155116 A1 | 5/2020 | Donhowe et al. |
| 2020/0170623 A1 | 6/2020 | Averbuch |
| 2020/0170720 A1* | 6/2020 | Ummalaneni ............ G06T 7/74 |
| 2020/0179058 A1 | 6/2020 | Barbagli et al. |
| 2020/0188038 A1 | 6/2020 | Donhowe et al. |
| 2020/0205903 A1 | 7/2020 | Srinivasan et al. |
| 2020/0205904 A1 | 7/2020 | Chopra |
| 2020/0214664 A1 | 7/2020 | Zhao et al. |
| 2020/0222666 A1 | 7/2020 | Chan et al. |
| 2020/0229679 A1 | 7/2020 | Zhao et al. |
| 2020/0242767 A1 | 7/2020 | Zhao et al. |
| 2020/0261175 A1 | 8/2020 | Fenech |
| 2020/0268240 A1 | 8/2020 | Blumenkranz et al. |
| 2020/0275860 A1 | 9/2020 | Duindam |
| 2020/0289023 A1 | 9/2020 | Duindam et al. |
| 2020/0297442 A1 | 9/2020 | Adebar et al. |
| 2020/0297444 A1* | 9/2020 | Camarillo ............. G16H 30/40 |
| 2020/0305983 A1 | 10/2020 | Yampolsky et al. |
| 2020/0315554 A1 | 10/2020 | Averbuch et al. |
| 2020/0330795 A1 | 10/2020 | Sawant et al. |
| 2020/0345436 A1 | 11/2020 | Kowshik et al. |
| 2020/0352427 A1 | 11/2020 | Deyanov |
| 2020/0352675 A1 | 11/2020 | Averbuch |
| 2020/0364865 A1 | 11/2020 | Donhowe et al. |
| 2020/0367726 A1 | 11/2020 | Landey et al. |
| 2020/0383750 A1 | 12/2020 | Kemp et al. |
| 2020/0391010 A1 | 12/2020 | Fenech et al. |
| 2020/0406002 A1 | 12/2020 | Romo et al. |
| 2021/0177370 A1* | 6/2021 | Robaina ............... A61B 5/0037 |
| 2021/0192759 A1* | 6/2021 | Lang ..................... G06T 3/40 |
| 2021/0307862 A1* | 10/2021 | Hayam .................... A61B 5/06 |

FOREIGN PATENT DOCUMENTS

| | | |
|---|---|---|
| CZ | 486540 | 9/2016 |
| CZ | 2709512 | 8/2017 |
| CZ | 2884879 | 1/2020 |
| EP | 3326551 A1 | 5/2018 |
| EP | 3367915 A4 | 7/2019 |
| EP | 3413830 A4 | 9/2019 |
| EP | 3576598 A1 | 12/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| MX | 03005028 A | 1/2004 |
| MX | 225663 B | 1/2005 |
| MX | 26292 | 2/2005 |
| MX | 246862 B | 6/2007 |
| MX | 265247 | 3/2009 |
| MX | 284569 B | 3/2011 |

* cited by examiner

SURGICAL TOOL NAVIGATION USING SENSOR FUSION

FIELD

This disclosure relates to the field of navigation of catheters and tools employing one or more sensors therein to improve navigation outcomes and provide greater specificity of location within the body of a patient.

BACKGROUND

Knowledge of surgical tool location in relation to the internal anatomy is important to successful completion of minimally invasive diagnostic and surgical procedures. A bronchoscope is the simplest form of navigation where a camera is placed at the distal tip of a catheter and is used to view the anatomy of the patient. Typically, the clinician uses their anatomic knowledge to recognize the current location of the bronchoscope. Near complex anatomic structures the clinician may attempt to compare pre-surgical patient images derived from computed tomography (CT), magnetic resonance imaging (MM), positron emissions tomography (PET) or ultrasound scans with the current images derived from the same imaging technology. Additionally, there are systems enabling the use of image processing techniques to recognize the current location of the distal tip. These systems can reduce the clinician's workload during navigation but have only achieved mixed results due to a lack of information such as orientation of the patient body and orientation of the camera.

Electromagnetic (EM) navigation is another more sophisticated system that utilizes a small sensor affixed to the tool distal tip creating a navigation catheter. The position of the EM sensor within an electromagnetic field around the patient body is detected and tracked as the navigation catheter is moved through the patient.

To assist EM navigation and enable the endoscopic, more particularly the bronchoscopic approach in the lungs, endobronchial navigation systems have been developed that use previously acquired MRI data or CT image data to generate a three-dimensional (3D) rendering, model or volume of the particular body part such as the lungs. The resulting volume generated from the MRI scan or CT scan is then utilized to create a navigation plan to facilitate the advancement of a navigation catheter (or other suitable medical device) through a bronchoscope and a branch of the bronchus of a patient to an area of interest. Following a registration of the patient to the navigation plan, a locating or tracking system, such an EM tracking system, may be utilized in conjunction with the navigation plan to facilitate guidance of the navigation catheter through the branch of the bronchus to the area of interest. In certain instances, the navigation catheter may be positioned within one of the airways adjacent to, or within, the area of interest to provide access for one or more medical instruments such as biopsy needles, ablation devices, and the like.

While these systems have proven successful and indeed have changed the standard of practice for lung biopsy and treatment, improvements are always desired.

SUMMARY

One aspect of the disclosure is directed to a system for navigation of a luminal network including: a navigation catheter, the navigation catheter including a sheath, an optical sensor, and an inertial measurement unit (IMU); a computer including a computer readable recording medium storing thereon an application that when executed by a processor executes steps of: capturing images via the optical sensor, comparing the captured images to pre-operative images stored in the computer readable recording medium and accessible to the application, identifying fiducials in the captured images that correspond to fiducials in the pre-operative images, receiving signals representative of acceleration and velocity of the IMU, and depicting the position of the catheter on a user interface including a three-dimensional (3D) model or two-dimensional (2D) images derived from the pre-operative images.

Implementations of this aspect of the disclosure may include one or more of the following features. The system where the processor executes a step of updating the depicted position of the catheter in the 3D model or 2D images based on received signals of the IMU. The system where the catheter includes a shape sensor, which may be a Fiber-Bragg grating. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

A further aspect of the disclosure is directed to a navigation catheter including: an outer sheath, an optical sensor for capturing images of a luminal network in which the sheath is placed, and an inertial monitoring unit (IMU) formed in a distal portion of the outer sheath, where the IMU is configured to output a one or more signals representing velocity and acceleration of the distal portion of the outer sheath as it is moved in the luminal network.

Implementations of this aspect of the disclosure may include one or more of the following features. The navigation catheter further including a working channel configured to receive one or more tools. The navigation catheter where the tools are a biopsy needle or an ablation device. The navigation catheter further including a shape sensor. The navigation catheter where the shape sensor is Fiber-Bragg grating. The navigation catheter where the shape sensor is in communication with the optical sensor.

Yet another aspect of the disclosure is directed to a method of navigating a catheter in a luminal network including capturing images via an optical sensor, comparing the captured images to pre-operative images. The method of navigating also includes identifying fiducials in the captured images that correspond to fiducials in the pre-operative images. The method of navigating further includes depicting the position of the catheter in a three-dimensional (3D) model or two-dimensional (2D) images derived from the pre-operative images. The method of navigating further includes detecting movement of a distal portion of the catheter via an inertial measurement unit (IMU) and updating the position of the catheter in the 3D model or 2D images based on the detected movement. Other embodiments of this aspect include corresponding computer systems, apparatus, and computer programs recorded on one or more computer storage devices, each configured to perform the actions of the methods and systems described herein.

Implementations of this aspect of the disclosure may include one or more of the following features. The method further including detecting a gravity vector from an inertial measurement unit (IMU). The method further including determining the orientation of the catheter. The method further including detecting a velocity and acceleration of the IMU. The method further including determining movement caused by ventilation or heartbeat. The method further including displaying on a user interface a representation of the ventilation rate or the heartbeat. The method further including detuning the update of the user interface to eliminate the determined movement caused by ventilation or heartbeat from the depicted position of catheter. The method where the catheter includes a shape sensor and depicting the position of the catheter is based in part on matching the shape of the sensor to shapes in the 3D model. Implementations of the described techniques may include hardware, a method or process, or computer software on a computer-accessible medium, including software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

BRIEF DESCRIPTION OF THE DRAWINGS

Various exemplary embodiments are illustrated in the accompanying figures. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

DETAILED DESCRIPTION

Figure 1:
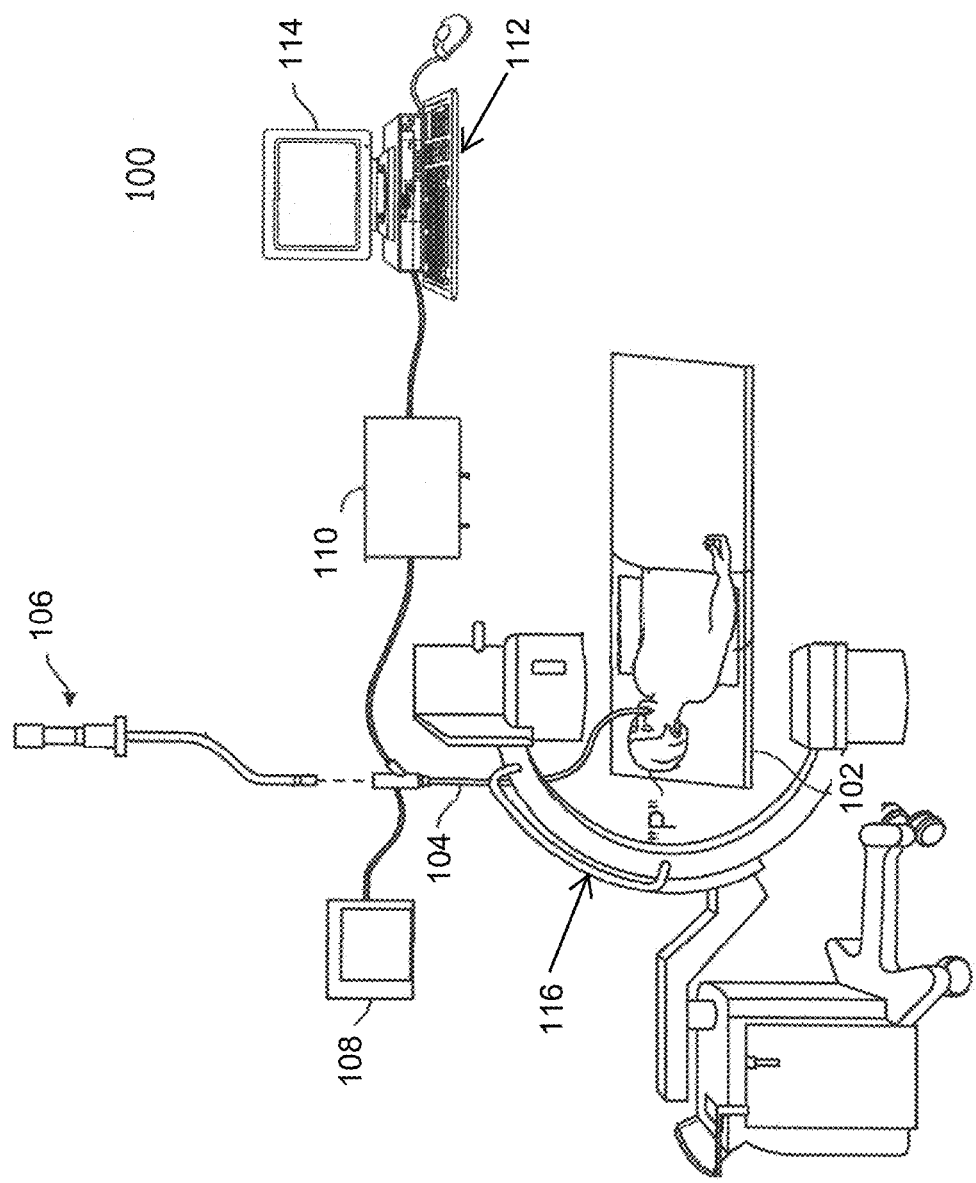
FIG. 1 is a schematic illustration of a system in accordance with the disclosure.

The disclosure is directed to a system and method for navigation of luminal networks such as the airways of the lungs. In one aspect of the disclosure, a catheter includes an optical sensor which generates images (e.g., a bronchoscope), and one or more additional sensors. These additional sensors may be a shape sensor such as Fiber-Bragg grating, or an inertial measurement unit (IMU). By utilizing these additional sensors in combination an optical sensor navigation of the luminal network can be undertaken without the need for an EM sensor system and an EM field generator. The disclosure is further directed to a variety of imaging techniques for use either in conjunction with pre-operative imaging and pathway planning or as an alternative to pre-operative pathway planning.

A Fiber-Bragg grating is a type of sensor that utilizes an optical fiber which includes a grating structure formed on the fiber. By analyzing the reflected patterns of light traversing the optical fiber a determination of the strain placed on the fiber can be made. Utilizing the detected strain, a determination of the shape of the body in which the optical fiber has been incorporated can be made. Thus, when a catheter with a Fiber-Bragg grating optical fiber is manipulated, the shape of the catheter can be sensed, and displayed on a user interface. In many applications where the catheter cannot be seen (e.g., lung navigation) the detected shape can be utilized to determine where in the luminal structure the catheter is located by comparing the shape of the sensor to the shapes of a three-dimensional model of the luminal structure.

An IMU is another type of sensor and typically includes one or more accelerometers, and one or more gyroscopes. Additionally, an IMU may include one or more of a magnetometer, a pressure sensor, and other types of sensors. An IMU provides individual velocity and acceleration measurements in the X, Y, and Z directions as well as roll about the X, Y, and Z axes. Using trigonometric operations, these measurements can be converted into a directional vector showing which way the IMU is moving. Combining two vectors allows for calculation of distance traveled. While the effects of gravity need to be compensated for at all times, the gravity vector can be used to identify the orientation of the sensor.

A common application for an IMU is in a phone or vehicle navigation system. The IMU for example, allows for a Global Positioning Satellite (GPS) system to continue operating even when the vehicle is in a tunnel or is otherwise prevented from acquiring a signal from the GPS receiver. The IMU provides position updates to the vehicle navigation system based on the IMU's sensed speed and acceleration until such time as a GPS signal is reacquired.

Another application of an IMU is for direct measurement of distances. By identifying a starting point, and sensing acceleration and angular variation to a second point, the IMU, and more particularly an application running on a measurement device, which might be a camera application, can determine the distance between the two points. For some of these applications the IMU may be configured as a small microchip measuring as little as 2 mm×2 mm in size and less than 1 mm in thickness. As will be appreciated, such a small size makes IMUs very useful in medical navigation applications in accordance with the disclosure. However, other size devices may be employed without departing from the scope of the disclosure.

An optical sensor may be, for example, a charge coupled device (CCD) or a complementary metal-oxide-semiconductor (CMOS) device. These devices may be analog or digital and enable the capture of light and other forms of electromagnetic radiation and convert them to electrical signals that can be converted into images. Additionally or alternatively, the optical sensor may employ one or more optical fibers or light pipes enabling the traversal of light into or out of a device in which the optical sensor is located. Indeed, though generally depicted as located at a distal end of a catheter, the present disclosure is not so limited, and the optical sensor may be located more proximally. For example, the optical sensor may also be offset back from the distal tip to allow viewing of the distal tip itself within the captured image. This allows for imaging and viewing of the deployment of tools or verifying the distal tip articulation. In addition, such an arrangement may compensate for reduced distal tip diameters that cannot accommodate an optical sensor and a working channel. Further, the optical sensor may be connected to one or more optic fibers to acquire or transmit the light or electromagnetic radiation at various wavelengths for illumination and for imaging. Further, one or more filters may be employed to improve or alter the light acquired and therewith the resolution of the images captured by the optical sensor.

FIG. 1 is a perspective view of an exemplary system 100 in accordance with the disclosure. System 100 includes a table 102 on which a patient P is placed. A catheter 104 is inserted into an opening in the patient. The opening could be a natural opening such as the mouth or nose. Alternatively, the opening may be formed in the patient, for example a surgical port. The catheter 104 may be a bronchoscope including one or more optical sensors for capturing live images and video as the catheter 104 is navigated into the patient P. One or more tools 106, such as a biopsy needle, ablation needle, clamp or others may be inserted into the catheter 104 for diagnostic or therapeutic purposes. A monitor 108 may be employed to display images captured by the optical sensor on the catheter 104 as it is navigated within the patient P.

The system 100 includes a locating module 110 which receives signals from the catheter 104, and processes the signals to generate useable data, as described in greater detail below. A computer 112, including a display 114 receives the useable data from the locating module 110, and incorporates the data into one or more applications running on the computer 112 to generate one or more user-interfaces that are presented on the display 114. Both the locating module 110 and the monitor 108 may be incorporated into or replaced by applications running on the computer 112 and images presented via a user interface on the display 114. Also depicted in FIG. 1 is a fluoroscope 116 which may be employed in one or more methods as described in greater detail below to construct fluoroscopic based three-dimensional volumetric data of a target area from 2D fluoroscopic images. As will be appreciated the computer 112 includes a computer readable recording medium such as a memory for storing image data and applications that can be executed by a processor in accordance with the disclosure to perform some or all of the steps of the methods described herein.

Figure 2:
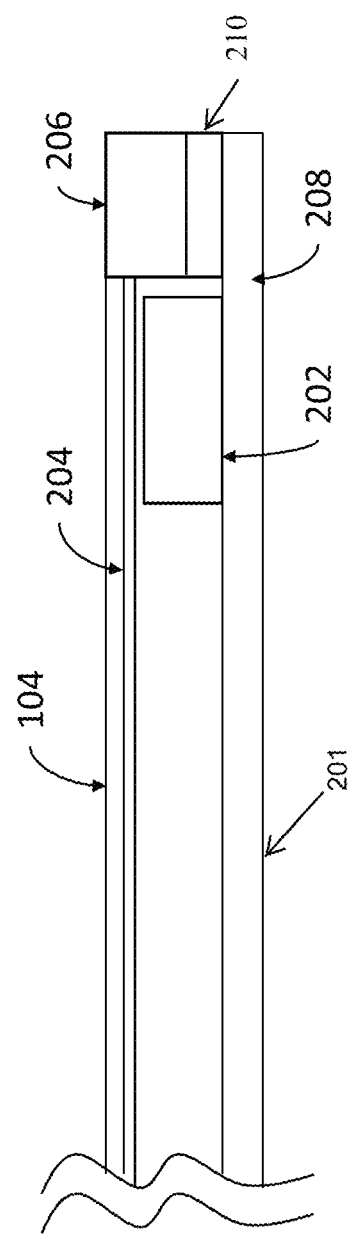
FIG. 2 is a schematic illustration of a distal portion of a catheter in accordance with the disclosure.

FIG. 2 depicts a further aspect of the disclosure related to the sensors that may be employed in connection with the catheter 104. In FIG. 2, the distal portion of the catheter 104 is depicted. The catheter 104 includes an outer sheath 201. A variety of sensors may be included in the distal portion of the catheter 104 including an IMU 202, a shape sensor 204, and an optical sensor 206 (e.g., a camera). In additional ultrasound sensors such as endobronchial ultrasound (EBUS) or radial endobronchial ultrasound (REBUS) may be employed. In one embodiment, one or more EBUS or REBUS sensors 210 may be placed proximate the distal portion of the catheter 104. In one embodiment they are placed in a distal face of the catheter 104 Though FIG. 2 depicts all three of these sensors installed in catheter 104, not all three are required in accordance with the disclosure. Also shown in FIG. 2 is a working channel 208 through which one or more tools 106 may pass to acquire a biopsy, perform an ablation, or perform another medical function, as required for diagnosis and therapy. As shown in FIG. 2, the shape sensor 204, which may be an optic fiber such as a Fiber-Bragg grating, described above, may connect with and be integrated into the optical sensor 206, such that the same optical fiber which carries the light captured by the optical sensor 206 is also utilized for shape sensing. The optical fiber forming the shape sensor 204 may be a single or a multi-core fiber as is known to those of ordinary skill in the art.

There are known in the art a variety of pathway planning applications for pre-operatively planning a path through a luminal network such as the lungs or the vascular system. Typically, a pre-operative image data set such as one acquired from a CT scan or an MRI scan is presented to a user. The target identification may be automatic, semi-automatic, or manually, and allows for determining a pathway through patient P's airways to tissue located at and around the target. In one variation the user scrolls through the image data set, which is presented as a series of slices of the 3D image data set output from the CT scan. By scrolling through the images, the user manually identifies targets within the image data set. The slices of the 3D image data set are often presented along the three axes of the patient (e.g., axial, sagittal, and coronal) allowing for simultaneous viewing of the same portion of the 3D image data set in three separate 2D images.

Additionally, the 3D image data set (e.g., acquired from the CT scan) may be processed and assembled into a three-dimensional CT volume, which is then utilized to generate a 3D model of patient P's airways by various segmentation and other image processing techniques. Both the 2D slices images and the 3D model may be displayed on a display 114 associated with computer 112. Using computer 112, various views of the 3D or enhanced 2D images may be generated and presented. The enhanced two-dimensional images may possess some three-dimensional capabilities because they are generated from the 3D image data set. The 3D model may be presented to the user from an external perspective view, an internal "fly-through" view, or other views. After identification of a target, the application may automatically generate a pathway to the target. In the example of lung navigation, the pathway may extend from the target to the trachea, for example. The application may either automatically identify the nearest airway to the target and generate the pathway, or the application may request the user identify the nearest or desired proximal airway in which to start the pathway generation to the trachea. Once selected, the pathway plan, three-dimensional model, and 3D image data set and any images derived therefrom, can be saved into memory on the computer 112 and made available for use in combination with the catheter 104 during a procedure, which may occur immediately following the planning or at a later date.

Still further, without departing from the scope of the disclosure, the user may utilize an application running on the computer 112 to review pre-operative 3D image data set or 3D models derived therefrom to identify fiducials in the pre-operative images or models. The fiducials are elements of the patient's physiology that are easily identifiable and distinguishable from related features, and of the type that could typically also be identified by the clinician when reviewing images produced by the optic sensor 206 during a procedure. As will be appreciated these fiducials should lay along the pathway through the airways to the target. The identified fiducials, the target identification, and/or the pathway are reviewable on computer 112 prior to ever starting a procedure.

Though generally described herein as being formed pre-operatively, the 3D model, 3D image data set and 2D images may also be acquired in real time during a procedure. For example, such images may be acquired by a cone beam computed tomography device, or through reconstruction of 2D images acquired from a fluoroscope, without departing from the scope of the disclosure.

In a further aspect of the disclosure, the fiducials may be automatically identified by an application running on the computer 112. The fiducials may be selected based on the determined pathway to the target. For example, the fiducials may be the bifurcations of the airways that are experienced along the pathway.

A further aspect of the disclosure is related to the use of linear EBUS and REBUS ultrasound sensors 210 described briefly above. In accordance with the ultrasound aspects of the disclosure a liner EBUS sensor may be placed in the distal face of the catheter 104. The result are forward looking ultrasound images can be acquired as the catheter 104 is navigated towards the target. Additionally or alternatively, the ultrasound sensors 210 are REBUS sensors, a 360 degree surrounding view of the distal portion of the catheter 104 can be imaged. Whether REBUS or EBUS, the sensors 210 can be used much like optical sensors to identify fiducials. Further, the images generated by the ultrasound sensors 210 can be compared to virtual ultrasound images generated from pre-procedure CT or MRI images to assist in confirming the location of the ultrasound sensor 210 (and catheter 104 therewith) while navigating towards the target.

Figure 3:
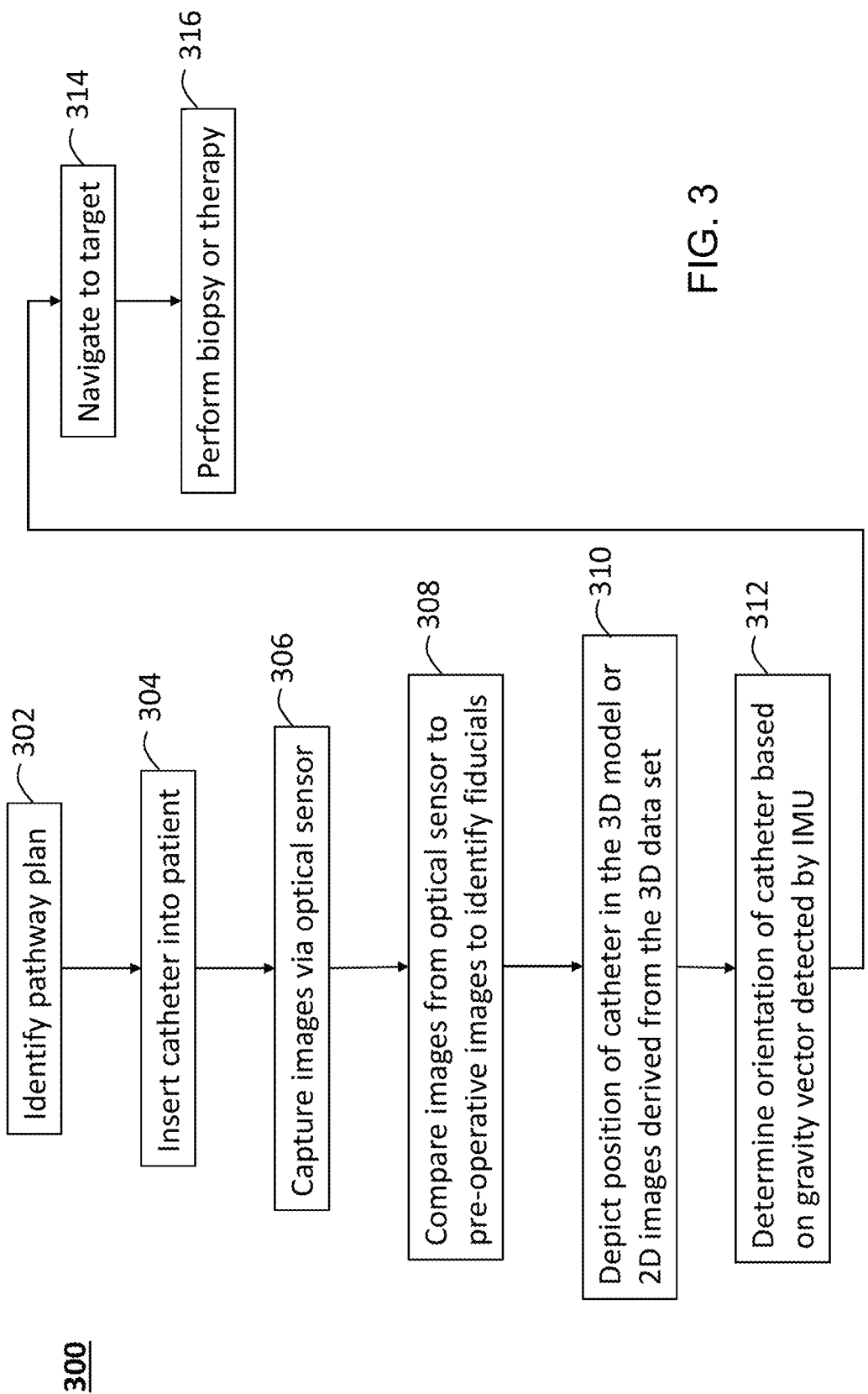
FIG. 3 is a flow chart detailing a method in accordance with the disclosure.

With respect to FIG. 3, a method 300 is now described for performing a registration of a pre-operative 3D image data and the 3D model derived therefrom with a patient using a catheter 104. At step 302, a pathway plan for a particular patient is identified in the memory of the computer 112 and presented on the display 114 in one or more user interfaces. At step 304 the catheter 104 including an optical sensor 206 is inserted into a patient P as depicted in FIG. 1 and navigation initiated. Either before or immediately following insertion of the catheter 104 imaging is initiated. Images are continually captured (e.g., a video) by the optical sensor 206 at step 306. During navigation, an application running on the computer 112 continually compares the images captured by the optical sensor 206 with the 3D model and 2D images derived from the 3D image data set. The images are compared to identify the fiducials, which were previously identified 3D image data set, in the images captured by the optical sensor 206.

Upon approaching a fiducial which had been identified during the pre-operative planning, described above, such as the main carina, a bifurcation, or other viewable feature, the images captured by the optical sensor 206 are compared to the 3D model and 2D images derived from the 3D image data set of the airways at step 308. This comparison may be automated where an application running on the computer 112 produces a user interface in which either or both the images from the optical sensor 206 or images generated from the 3D model are presented in a user interface on display 114 at step 310.

As part of this comparison, a rough measurement of the distance of the optical sensor 206, and thus the catheter 104, from the fiducial can be made based on the limited focal length of the optical sensor 206. The image may be filtered with a sharpening filter and a ratio of the image before and after being passed through a sharpening filter gives an estimate of the distance from the focal point to the fiducial. The size of the fiducial in the image defines the distance of the fiducial from the sensor 206. If the object is more proximal to the camera the fiducial will appear (larger) or more distal (smaller). In this manner, the application can identify the fiducial in both the images from the optical sensor 206 and in the 3D model or the 3D image data set and determine approximately the distance of the catheter 104 from that fiducial so that a displayed image of 3D model or 2D images from the 3D image data set can updated to substantially correspond to the image from the optical sensor 206.

In one alternative, the application may request that the user confirm in the user interface that an identified fiducial found in the 3D model or 2D images derived from the 3D image data set and a the fiducial seen in the image captured by the optical sensor indeed correspond. Alternatively, the user interface may present the image from the optical sensor 206 and enable the user to navigate through the 3D model to a point where the image derived from the 3D model substantially corresponds to the image from the optical sensor.

Regardless of which alternative is employed, the result of step 310 is that the application presents a view on the user interface in which the position of the catheter 104 and optical sensor 206 in the 3D model or 2D images derived from the 3D data set. As described above, this position is based on the identification of the fiducials in the images from the optical sensor 206.

At step 312, once a match between a set of fiducials in the images from the optical sensor 206 and those in the 3D model or 3D image data set is made, the patient body orientation may be determined based on the gravity vector output by the IMU 202. While the patient is typically laying on their back, this is not always the case, but regardless the gravity vector will generally be directed towards to operating table 102. Once this has been detected, the application can adjust the presentation of the 3D model and 2D images derived from the 3D image data set to accommodate the determination of the gravity vector and the registration process is completed. The user interface presents an accurate indication of the location of the catheter 104 in the patient with reference to the 3D model or 2D images derived from the 3D image data set.

In a further aspect of the disclosure, following registration, the pathway plan, which may be presented as a pathway or ribbon to follow for navigation to the target may be presented in the user interface on the images captured from the optical sensor 206. Thus, once registered, a user could simply follow the pathway as it appears in the live images from the optical sensor 206 to navigate to the target.

Further, in combination with developing a pathway plan and registration of the position of the catheter 104 in the body with the pre-operative imaging and 3D models as described above, the signals received from the IMU 202 can be processed by the computer 112 and an application running thereon to present alignment and trajectory information in the user interface. This alignment and trajectory information may be displayed in conjunction with the pathway to the target identified in the pre-operative images. Because of the gravity vector measurement available from the IMU 202, specific pathway approaches can be designed in the pathway planning procedure that allow for target access from an anterior or posterior approach to any given target.

Following registration, navigation to the target commences at step 314. Sequential changes in the measurements captured by the IMU 202 indicate changes in position of the IMU 202 and therewith the catheter 104. These changes in position can be presented on the user interface of the display 112 such that the IMU 202 provides tracking of the catheter 104 as it is navigated within the patient. The IMU 202 is usually sufficiently sensitive to detect not just advancement and rotation of the catheter 104 but also involuntary motions caused by breathing and heartrate. In one embodiment, the type of motion is determined through comparison of the movement direction detected by the IMU 202 in relation to the change in the image from the optic sensor 206. With advancement of the catheter 104 there will generally be commensurate change in the size of objects in the images generated by the optical sensor 206, these changes can be compared to confirm the advancement or retraction of the catheter 104. Rotation of the catheter 104 will generally result in a change in orientation of successive images generated by the optical sensor 206, but little or no change in detected movement from the IMU 202. Conversely, patient motion caused by breathing and heart will generally have little or no change in view, despite detected movements by the IMU 202.

The separation of the cause of motion and the ability to sense other physiological data can be useful to a user during a procedure. For example, using the methods described above, the motion caused by the beating of the heart can be detected. While the motion caused by this heartbeat may be something that it is desirous to remove from the displayed images from the optical sensor 206 and from changes in location in the 3D model, the recording of the heart rate can nonetheless be performed without requiring additional sensors. Further, additional movement of the catheter 104 caused by more local arterial pulse may also be detected to provide an indication of proximity to, or in contact with, certain critical structures such as major arteries or veins, either to be avoided or as the intended target.

Similarly, the movement caused by ventilation can be tracked. Again, while this movement may be something that is removed from the displayed images from the optical sensor 206, this data can be monitored to confirm the state of the patient. Monitoring this motion, predictions can be made as to where in the body the distal portion of the catheter 104 is at any particular time during ventilation. Because it is important in the collection of a biopsy or insertion of an ablation probe into a tumor for treatment that the probe or biopsy needle actually be inserted into the tumor or lesion, monitoring the changes in position of the catheter 104 caused by ventilation can provide an accurate indication of the timing (e.g., where in the cycle) required for successful insertion of the biopsy needle or ablation tool and when the working channel of the catheter 104 is indeed facing the target so that a successful biopsy or placement of an ablation probe can be achieved. Thus, following navigation proximate a target identified in the pre-operative images (e.g., within 2-3 cm) the biopsy needle or ablation tool can be deployed through the working channel 208 to perform biopsy or therapy of the target at step 316.

Further, this data related to movement of the catheter 104, and particularly the IMU 202 can be displayed in a user interface on display 114 to provide an indication of heartbeat and ventilation rate to the user. Still further, in instances where the ventilation rate is relatively constant this data can be used to provide an indication of the timing of when a biopsy or insertion of a treatment device into a tumor should be undertaken. As a practical matter, the movement caused by the heat beat is rapid, but small and can be accurately measured by the IMU 202. In contrast, the movements caused by ventilation are larger and of longer duration. By collecting data related to motion caused by these two physiological functions, a timing diagram may be generated and displayed in a user interface on display 114. The timing diagram may be associated primarily with the ventilation rate, and particularly within some range of the end of exhalation or the end of inspiration. In one embodiment, the indication of an appropriate time to perform the biopsy may be triggered (turned on or displayed) when it is determined that the movement of the IMU 202 indicates that inspiration is within some percentage of being complete or having been completed (e.g., 15% before or after completion of inspiration). It is within this range that the remaining movement of the target as a result of ventilation is sufficiently small that the likelihood of achieving a useful biopsy or placement of a treatment device is highest. A similar range may be used around the end of exhalation. The user interface may for example present the ventilation rate as a sinusoidal wave, with the waveform having a different color when approaching the end of inspiration or exhalation, the different color signaling an appropriate time to acquire the biopsy or place the treatment device. This signaling may also be integrated with the data relating to movement caused by the heartbeat, and in one example the indicator of when the perform the biopsy may pulse at the same frequency as the heart rate, and provide an indication to perform the biopsy or treatment device insertion at a desired time related to the heartbeat. In one example this may be at a period between the contraction of ventricles (i.e. the which are a primary cause of motion associated with an individual heartbeat.

Still a further aspect of the disclosure relates to the collection of movement data by the IMU 202 at different points along a planned pathway. As the IMU 202 is moved, the user interface may indicate that movement of the catheter 104 should be stopped for a few seconds. By stopping periodically to collect data regarding movement caused by ventilation and heartbeat at that location an estimate can be made of the movement caused by ventilation and heartbeat at every location along the pathway. With this information, and a determination of the movement of the IMU once it is withing about 3 cm of the target, an estimate of the movement of the target relative to the position of the end of the catheter 104 (i.e., the IMU) can be calculated and employed in conjunction with the timing algorithm described above.

In accordance with another aspect of the disclosure, the data relating to the motion of the IMU 202 can be analyzed by an application on the computer 112 to determine the speed of movement of the catheter 104. It may be desirable to determine when the catheter 104 is moving too quickly for a given environment. For example, when the catheter 104 in navigating portions of the airways with a diameter is similar to or even smaller than the diameter of the catheter 104, the catheter 104 may rub against the airway walls. If the catheter 104 is moved too quickly while rubbing or otherwise contacting the airways walls the airway wall cilia may be damaged. Thus, determination of the velocity of the catheter 104 and alerting a user via a user interface on display 114 can alert a user to the potential for damage and direct a reduction in speed of the catheter 104.

In accordance with an aspect of the disclosure, the IMU 202 may periodically experience drift. That is its detected position may develop inaccuracies with time. To compensate for the inaccuracy, fiducial identification with the optical sensor 206 and comparison to 3D model may be continuously performed during the navigation process. Thus, at each new fiducial, the location of the IMU 202 and optical sensor 206 is updated to correct for any drift or inaccuracy that may have developed since navigating past the preceding fiducial. In one aspect of the disclosure this works as a registration correction or confirmation step each time the catheter 104 approaches a fiducial within the patient.

In accordance with a further aspect of the disclosure the application on the computer 112 can utilize the gravity vector of the IMU 202 to compensate for rotation of an image generated by the optical sensor 206 such that the displayed image on the user interface represents "up" as anterior to the patient at all times, regardless of the orientation of the optical sensor 206 within the patient. Further, when the catheter 104 is embodied as an endoscope, endoscope controls which can be manipulated to control the shape and orientation of a distal portion of the catheter can also be adjusted by the relationship between the gravity vector detected by the IMU 202. As a result, physician inputs are translated appropriately and result in desired movement of the catheter within the patient can be accurately anticipated by the user when referencing the pre-operative images or the 3D model.

The IMU 202 can also be used for crash detection of the catheter, particularly in instances where the optical sensor 206 may not be providing adequate images. Crash detection can refer to impact, or contact with tissue. Typically, as a catheter 104 is navigating through the patient the movements will be within a range of velocity and acceleration and velocity. If, however, there is an abrupt change or cessation in movement or a sudden lateral perturbation, these changes can result in an inference that there was a crash of the catheter 104 with an airway wall or other object within the lung. In some instances the IMU 202 and shape sensor 304, may be employed in combination to determine that there is no movement of the catheter 104 and that further movement is not possible even in instances where there is no sudden change in velocity or acceleration of the catheter 104.

As noted above, the catheter 104 may include a working channel 208 though which one or more tools including biopsy, ablation, and other therapy tools may be passed. However, catheter 104 may not be equipped with an open working channel 208, particularly for catheter's designed for navigation to the periphery of the lungs where the airways may be quite small. As a result, the optical sensor 206 itself may be located in a working channel of the catheter 104 and be removable therefrom. Removal of the optical sensor 206 frees the working channel and allows for one or more tools may now be inserted through the catheter 104. Once the optical sensor 206 is removed from the catheter 104 or following navigation into narrow airways such that the application is unable to consider the images from optical sensor 206 to determine whether the catheter 104 has moved. However, the IMU 202, which remains in the catheter 104 tracks the of motion vectors of the distal portion of the catheter 104. Thus, the position of the catheter 104 can be updated in the 3D model and images displayed in the user interface on the display 114 if the catheter 104 moves after removal of the optical sensor 206. The application running on the computer 112 may eliminate gravity and patient motion caused by breathing and heartbeat to identify actual changes in position of the catheter 104. If the position of the catheter 104 moves, relative to the position it was in when the optical sensor 206 was removed the user may manipulate the catheter 104 to correct the position of the catheter 104 prior to performing a biopsy or therapy. In some applications the user interface may automatically switch from presenting the images from the optical sensor 206 to only showing in the user interface the location of the catheter 104 in the 3D model or 2D images derived from the 3D image data set.

Because in many instances the catheter 104 will have been navigated 80-90% of the way to the target. And further because the navigation up to the point that the optical sensor 206 is no longer able to provide useable images has been confirmed by the processes described above, the user can have reasonable confidence that the "last mile" of navigation relying just on the data from the IMU 202 is sufficiently accurate. This last mile is typically in the range on only 2-5 cm in length. Still further, it is in this last mile navigation that the ability of the IMU to detect different sources of movement, and to effectively cancel or account for those sources of movement is most effective to successful navigation. As one example the signals received from the IMU 202 can actually be detuned so that the user interface does not show a rapid position change as a result of breathing and heart rate. This detuning allows data acquisition rate to remain high and the refresh rate to remain high for the display by subtracting the delta between anatomic induced motion and clinician induced motion from the total motion of the IMU 202.

Figure 4:
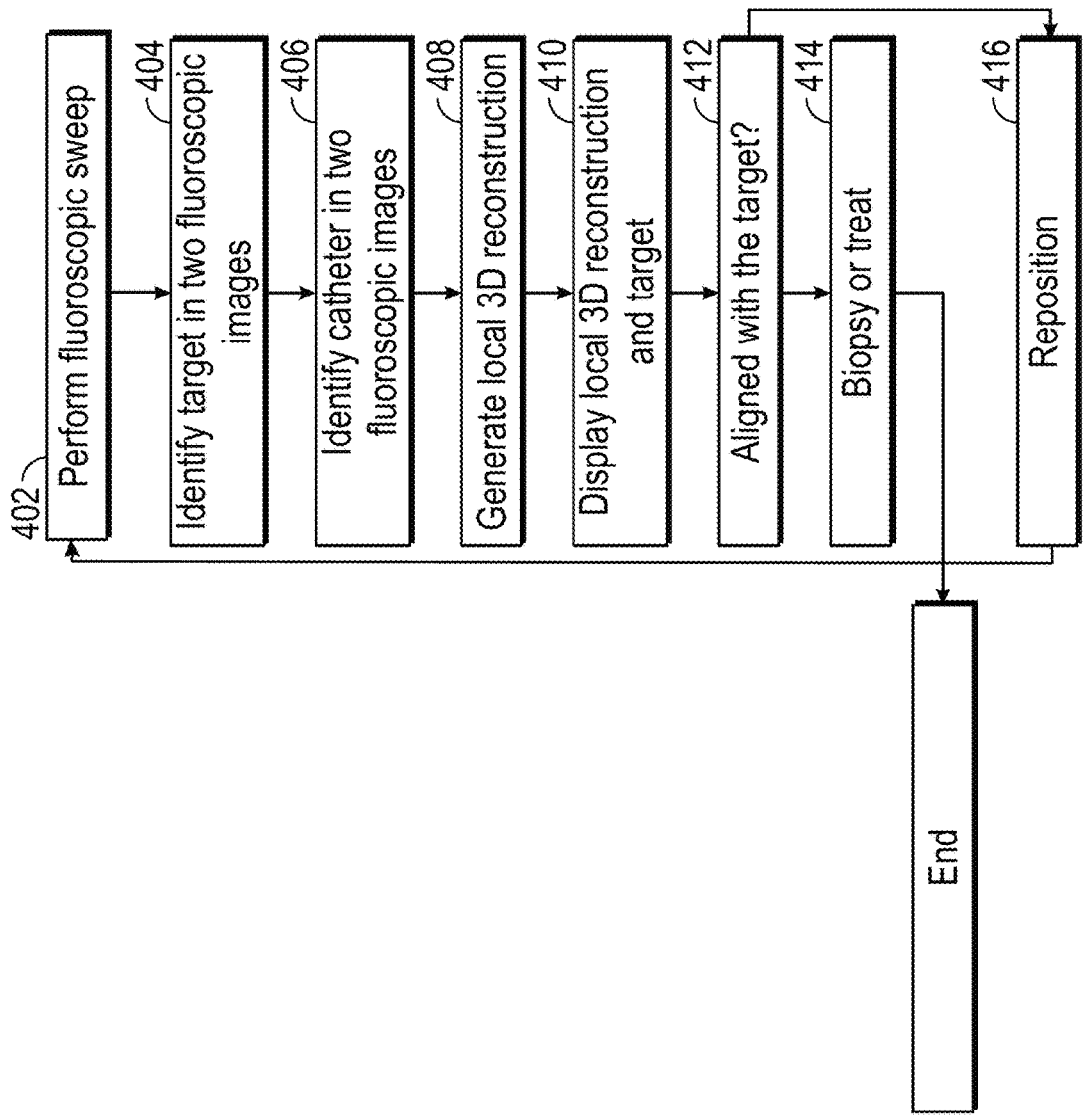
FIG. 4 is a flow chart detailing a further method in accordance with the disclosure.
Figure 5:
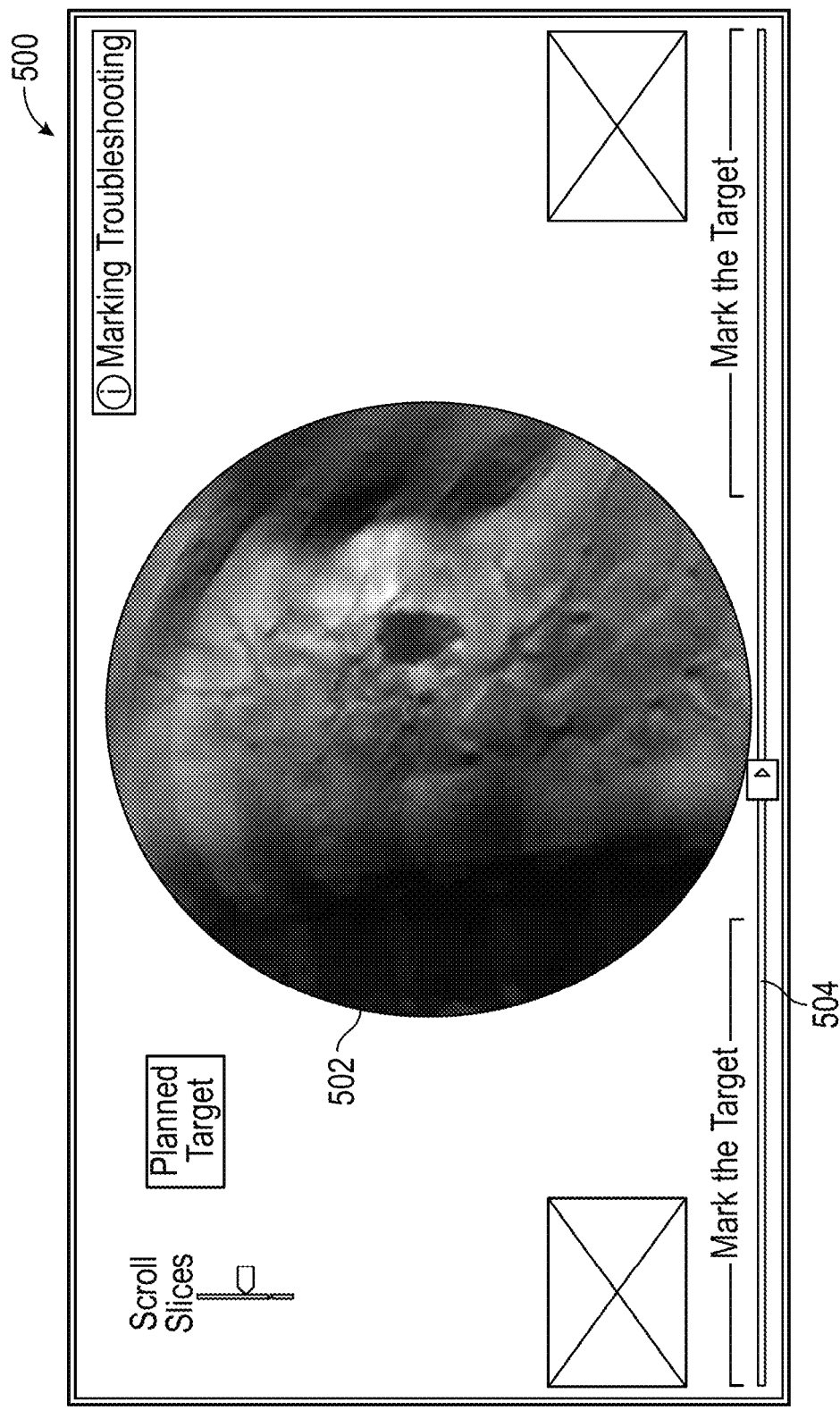
FIG. 5 is an illustration of user interface in accordance with the disclosure.
Figure 6:
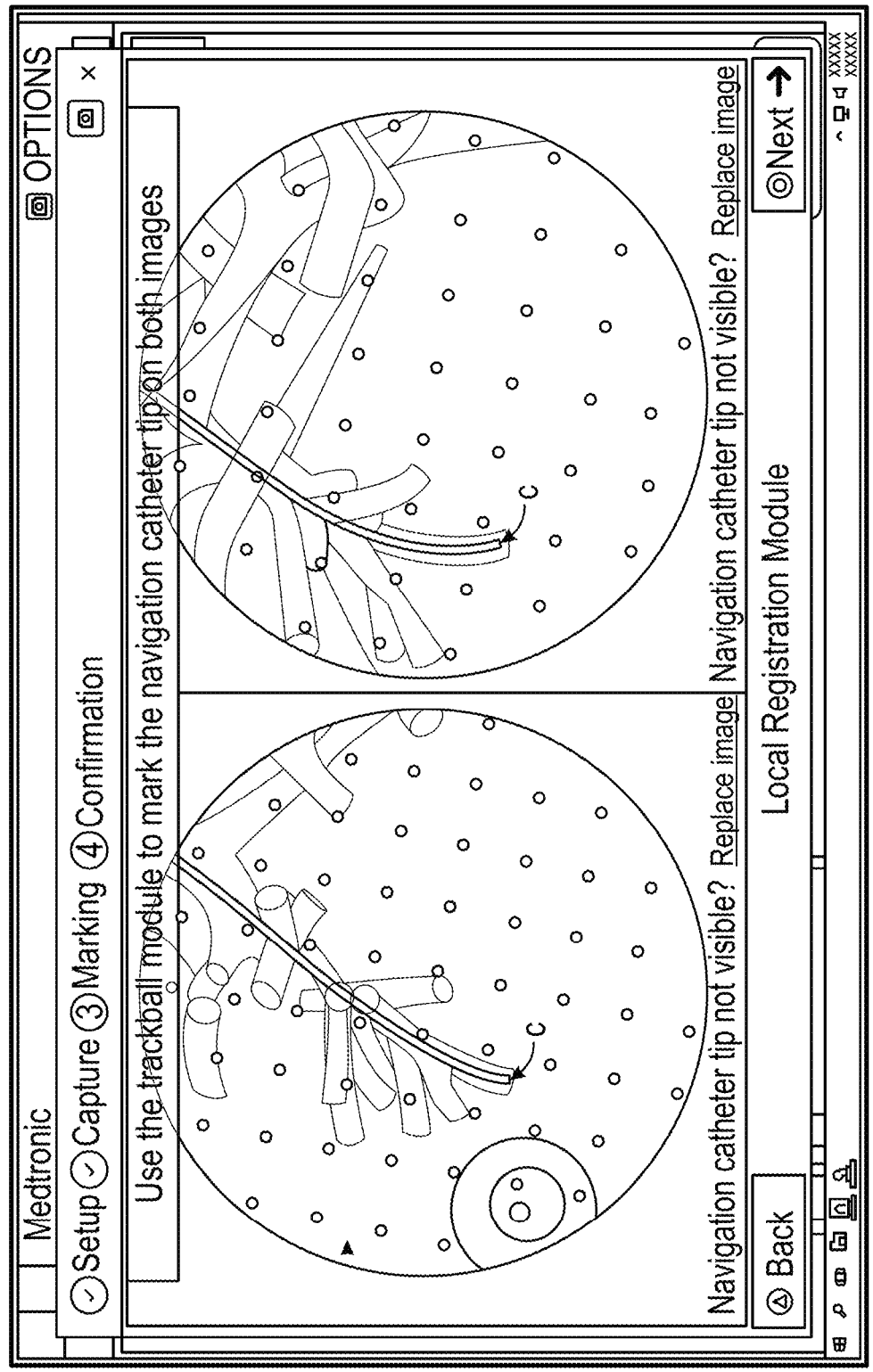
FIG. 6 is an illustration of a further user interface in accordance with the disclosure.

In addition to the updates in position that can be determined from the IMU 202, further confirmatory steps utilizing the fluoroscope 116 are also possible. Additionally, or alternatively a CBCT may be employed for these confirmatory steps. FIG. 4 describes a methodology for confirming the location of the catheter 104 relative to a target. Following navigation of the catheter 104 to a position believed to be proximate the target (e.g., within 2-5 cm), a fluoroscopic sweep may be undertaken at step 402 whereby fluoroscopic images of the patient P are acquired. These images may be in the form of a fluoroscopic video captured as the fluoroscope traverses an angle from 15-30 degrees on one side of the AP or 0° position to 15-30 degrees on the other side of the AP position. After the sweep is performed, the user interface may present the user with a fluoroscopic image and request the user to identify the target in the fluoroscopic image at step 404. An example of a user interface 500 that may be presented to the user is shown in FIG. 5 in which scrollable fluoroscopic images 502 are presented to the user. Once identified in one fluoroscopic image 502, the user interface allows the user to scroll using a scroll bar 504 to identify a second fluoroscopic image in which to identify the target. Alternatively, the application may search the fluoroscopic images and automatically identify the target. Similarly, a user interface 600 may present a user interface in which the user is to identify the end of the catheter "C" at step 406 and as shown in FIG. 6. This indication is received by the application at step 406.

Once the target and catheter 104 are identified in the fluoroscopic images, a 3D reconstruction can be generated at step 408 and displayed at step 410. This display of the 3D reconstruction includes a clear definition of the target marked in the fluoroscopic images of the fluoroscopic sweep. This provides an accurate indication of the location of the target, and the relative location of the catheter 104 and determinations can be made whether the catheter is aligned with the target as well as the distance to the target from the end of the catheter 104. The relative position data may be displayed on the user interface or the user may simply make the determination of alignment based on observation of the 3D reconstruction. If the target and the catheter 104 are aligned at step 412, the method may proceed to step 414 where a biopsy sample or a treatment is undertaken.

If it is determined that the tool and the target are not aligned the method proceeds to step 416 where the catheter 104 or tool is repositioned. After repositioning the method returns to step 402 to perform another fluoroscopic sweep. This procedure may be repeated as needed until alignment is achieved at step 412 and a biopsy or treatment can be undertaken at step 414.

A further aspect of the disclosure is directed to the use of a shape sensor 204. As noted above the shape sensor 204 may be one or more Fiber-Bragg grating optical fibers. As these flexible fibers are bent during navigation of the catheter 104 through a luminal network such as the airways of the lungs a strain measurement can be ascertained of the optical fiber by application of light through the fiber and analysis of reflected components of the light. This strain can be converted into a determination of the shape of the sensor 204 experiencing the strain. Accordingly, the addition of a shape sensor 204 to the catheter 104 provides a further set of data that can be analyzed in conjunctions with the data received from the IMU 202 and the optical sensor 206 to determine the location of the catheter 104 within the body of the patient. For example, the determined shape of the shape sensor 204 can be compared to the shapes of a 3D model derived from a pre-operative CT scan. This shape can be compared to the shape of all of the components of the 3D model to identify the closest matching physiology of the patient in the 3D model. This data may be used in conjunction with the location data derived from the IMU 202 to provide further accuracy.

The data from a shape sensor 204 may be particularly useful when navigating near the periphery of the lungs, wherein the optical sensor 206 provides less guidance. As airways get smaller it is increasingly difficult for optical sensors to provide useable information regarding movement and location. This lack of useable information provided by the optical sensor 206 is due narrowness of the airways providing little depth for the optical sensor 206 to discern movement. Further the tissue of the airways is largely uniform rendering it difficult to discern movement past any observable features of the airways. Indeed, it is difficult to discern whether the optical sensor 206 is moving through the airway, or whether the airway is moving past the optical sensor 206. As noted above, the sensed shape of the catheter 104 can be matched to the shape of the 3D model derived from the 3D image data set. Further, the shape sensor 204 can provide an orientation of the distal end of the catheter 104, which identifies a trajectory that a tool, such as a biopsy tool would follow if extended out the working channel of the catheter 104. These aspects can be rendered and displayed to a user in the user-interface in conjunction with the 3D model or 2D images derived from the 3D image data set. The shape sensor 204 can further be employed in conjunction with the IMU 202 to provide the correction for potential drift of the location of the IMU 202.

The shape sensor 204 also provides an opportunity to confirm that the catheter 104 remains on the planned pathway. By analyzing the shape of the catheter 104 and comparing it to the shape of a portion of the planned pathway, a confirmation that the catheter 104 remains on the planned pathway can be generated. If it is determined that the catheter 104 is not on the planned pathway, the application may generate an alternative pathway, or may simply present an alert to the user on the user interface.

Yet another aspect of the disclosure is directed to the generation of a 3D model based on the pathway navigated by the catheter 104. As the catheter 104 is navigated and optical sensor 206 captures images, these images can be collected in series creating an image stack. In addition, the IMU 202 and/or the shape sensor 204 collect data regarding movement and shape of structures that the catheter 104 passes through. These data can be combined to generate a 3D model. This 3D model may be generated without the use of a pre-operative CT or MM image. This may be useful for patients where there is a desire to limit exposure of the client to radiation, or for whom a such exposure is impossible. Further, this may be useful for patients who simply cannot access a CT or Mill machine based on their geography. In this way the catheter 104 may be used as an alternative to the CT or Mill and used to explore the airways of the patient.

A further use of this mapping the airways using the images derived from the optical sensor 206 and generation of a 3D model is to acquire data regarding the location in the patient where a biopsy was taken or where a therapy was applied. The user interface may include functionality where the user can mark the location of the biopsy or therapy relative to the 3D model that was generated during the actual navigation of the patient's airways. The same process can apply when using a 3D model or 2D images derived from the 3D image data set that was acquired pre-operatively. The 3D model with the indications of where biopsies and therapies have been undertaken can be saved to the computer 112 and ultimately become part of the patient's electronic medical record. These 3D models, can then be accessed at a later time and overlaid on new imaging (e.g., CT image data set or 3D model), as a point of comparison to make determinations such as whether the lesion in question has already been biopsied, whether areas that received therapy previously now show indications of a new lesion or other factors that can be relevant for the future treatment and management of the health of the patient.

Another aspect of the IMU 202 is that with its output a determination can be made regarding the orientation of the imaging surfaces of the optical sensor 206. Knowing the orientation of the optical sensor 206 enables an application running on the computer 112 to properly align the captured images with each other as the catheter 104 is driven through the airways of the patient. This ensures the proper orientation of the images when displayed despite the catheter 104 twisting and turning as it is being navigated through the airways.

From the foregoing and with reference to the various figure drawings, those skilled in the art will appreciate that certain modifications can also be made to the present disclosure without departing from the scope of the same.

Detailed embodiments of the present disclosure are disclosed herein. However, the disclosed embodiments are merely examples of the disclosure, which may be embodied in various forms and aspects. Therefore, specific structural and functional details disclosed herein are not to be interpreted as limiting, but merely as a basis for the claims and as a representative basis for teaching one skilled in the art to variously employ the present disclosure in virtually any appropriately detailed structure.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A system for navigation of a luminal network comprising:
   a navigation catheter, the navigation catheter including a sheath, an optical sensor, and an inertial measurement unit (IMU), the IMU mounted in a distal portion of the sheath;
   a computer including a computer readable recording medium storing thereon an application that when executed by a processor executes steps of:
   capturing images via the optical sensor;
   comparing the captured images to pre-operative images stored in the computer readable recording medium and accessible to the application;
   identifying fiducials in the captured images that correspond to fiducials in the pre-operative images;
   depicting a position of the navigation catheter on a user interface including a three-dimensional (3D) model or two-dimensional (2D) images derived from the pre-operative images;

receiving signals representative of acceleration and velocity of the IMU;

determining a body orientation of a patient from a gravity vector output by the IMU;

adjusting the depiction of the navigation catheter in the 3D model or the 2D images based on the determined body orientation; and controlling an orientation of a distal portion of the navigation catheter to account for the gravity vector output by the IMU.

2. The system of claim 1, wherein the processor executes a step of updating the depicted position of the navigation catheter in the 3D model or the 2D images based on received signals of the IMU.

3. The system of claim 2, wherein the navigation catheter further includes a shape sensor.

4. The system of claim 3, wherein the shape sensor is a Fiber-Bragg grating.

5. A navigation catheter comprising:
an outer sheath;
an optical sensor for capturing images of a luminal network in which the outer sheath is placed; and
an inertial monitoring unit (IMU) formed in a distal portion of the outer sheath, wherein the IMU is configured to output one or more signals representing velocity and acceleration of the distal portion of the outer sheath as the outer sheath is moved in the luminal network, wherein the optical sensor captures images and an application stored in a memory in communication with the navigation catheter receives the captured images, compares the captured images to pre-operative images, identifies fiducials in the captured images that correspond to fiducials in pre-operative images, determines a position of a distal portion the navigation catheter within the luminal network, depicts a representation of the navigation catheter at the determined position of the outer sheath in a three-dimensional (3D) model or two-dimensional (2D) images derived from the pre-operative images on a user interface, determines a body orientation of a patient from a gravity vector output by the IMU, adjusts the depiction of the navigation catheter in the 3D model or the 2D images based on the determined body orientation, and controls an orientation of the distal portion of the outer sheath to account for the gravity vector output from the IMU.

6. The navigation catheter of claim 5, further comprising a working channel configured to receive one or more tools.

7. The navigation catheter of claim 6, wherein the one or more tools are a biopsy needle or an ablation device.

8. The navigation catheter of claim 5, further comprising a shape sensor.

9. The navigation catheter of claim 8, wherein the shape sensor is Fiber-Bragg grating.

10. The navigation catheter of claim 8, wherein the shape sensor is in communication with the optical sensor.

11. A method of navigating a catheter in a luminal network comprising:
capturing images via an optical sensor on a catheter navigating the luminal network;
comparing the captured images to pre-operative images of the luminal network;
identifying fiducials in the captured images that correspond to fiducials in the pre-operative images;
depicting a position of the catheter in a three-dimensional (3D) model or two-dimensional (2D) images derived from the pre-operative images;
detecting movement of a distal portion of the catheter via an inertial measurement unit (IMU) mounted in the distal portion of the catheter;
determining a body orientation of a patient from a gravity vector output by the IMU;
adjusting the depiction of the catheter in the 3D model or the 2D images based on the determined body orientation; and
controlling an orientation of a distal portion of the catheter to account for the gravity vector output from the IMU.

12. The method of claim 11, further comprising determining an orientation of the catheter.

13. The method of claim 11, further comprising detecting a velocity and acceleration of the IMU.

14. The method of claim 13 further comprising determining a component of the movement caused by ventilation or heartbeat.

15. The method of claim 14, further comprising displaying on a user interface a representation of the ventilation or the heartbeat.

16. The method of claim 15, further comprising detuning an update of the user interface to eliminate the determined component of the movement caused by ventilation or heartbeat from the depicted position of the catheter.

17. The method of claim 11, wherein the catheter includes a shape sensor and depicting the position of the catheter is based in part on matching a shape of the shape sensor to shapes in the 3D model.

18. The method of claim 11, further comprising performing a fluoroscopic sweep and generating a fluoroscopic three-dimension (3D) volume.

19. The method of claim 18, further comprising determining the position of the catheter relative to a position of a target in the 3D volume.

* * * * *